US00PP16737P2

(12) United States Plant Patent
Pierce

(10) Patent No.: US PP16,737 P2
(45) Date of Patent: Jun. 27, 2006

(54) ***CALIBRACHOA* PLANT NAMED 'CAL ORAN'**

(50) Latin Name: ***Calibrachoa* spp.**
Varietal Denomination: Cal Oran

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 87 days.

(21) Appl. No.: 11/090,459

(22) Filed: Mar. 25, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Jondle & Associates P.C.

(57) ABSTRACT

A *Calibrachoa* cultivar particularly distinguished by its orange-colored flowers is disclosed.

1 Drawing Sheet

Figure 1:
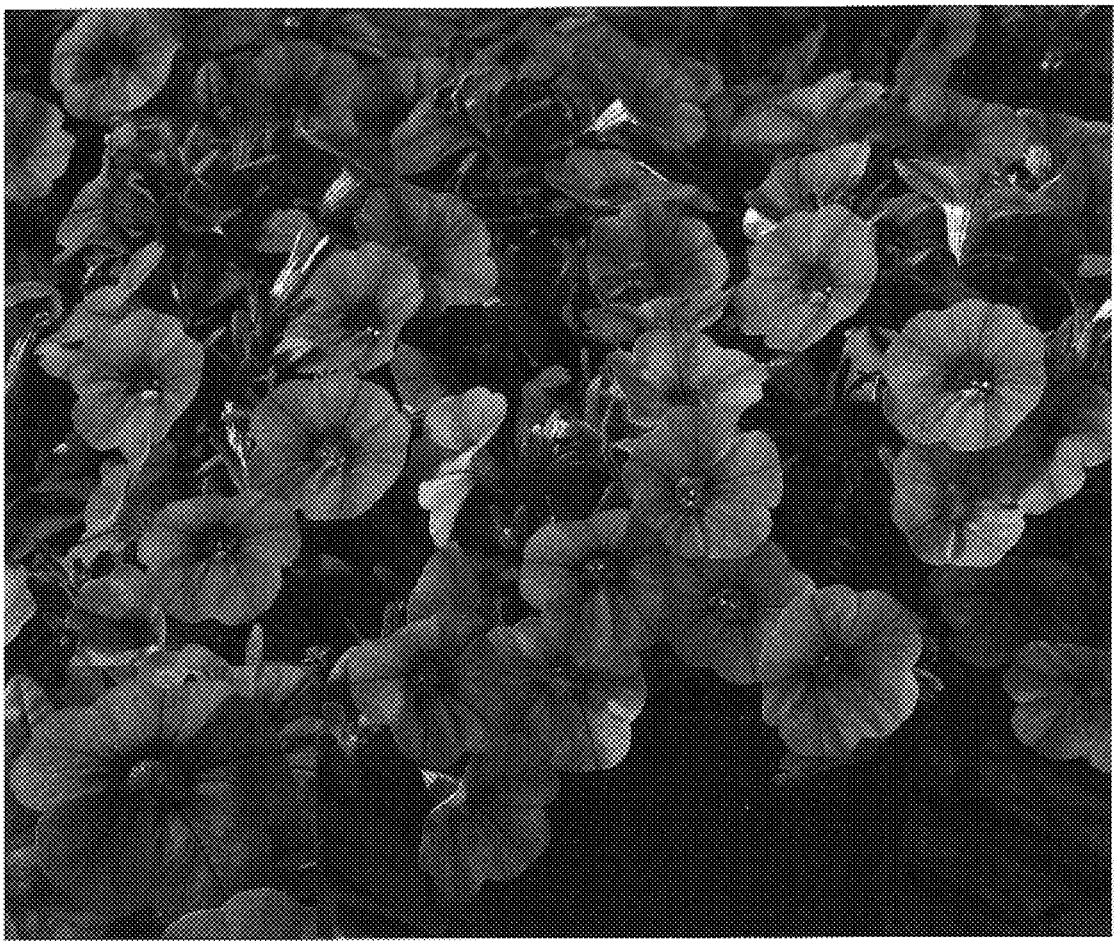

Genus and species: *Calibrachoa* spp.
Variety denomination: 'Cal Oran'.

BACKGROUND OF THE INVENTION

The present invention comprises a new and distinct cultivar of *Calibrachoa*, botanically known as *Calibrachoa* spp., and hereinafter referred to by the cultivar name 'Cal Oran'. The new cultivar originated from a hybridization made in the year 2001 in Gilroy, Calif. The female parent was proprietary *Calibrachoa* breeding line 367-1 (unpatented) with neon orange-rose flowers. The male parent was proprietary *Calibrachoa* breeding line 455-1 (unpatented) with coral-rose flowers. The new cultivar was created in 2001 in Gilroy, Calif. and has been asexually reproduced over a two-and-a-half year period by vegetative cuttings and tissue culture in Gilroy, Calif., Andijk, The Netherlands, and Guatemala. The plant has also been trialed at Gilroy, Calif., Litchfield, Mich. and Andijk, The Netherlands. The present invention has been found to retain its distinctive characteristics through successive asexual propagations. 'Cal Oran' reproduces true to type in successive generations of asexual reproduction.

Description of the genus *Calibrachoa* Llave & Lex

The genus *Petunia* was originally established in 1803 by A. L. Jussieu, who described both *P. parviflora* and *P. nyctaginiflora* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida*, the Garden *Petunia*, and the inter-relationship of several species classified as *Petunia*. These studies discovered that *P. hybrida* and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the *Petunia* genus, Wijsman and J. H. de Jong proposed transferring the 14 chromosome species to the genus *Stimoryne*. Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa*, originally established by Llave and Lexarza in 1825. *Calibrachoa paraviflora* (=*C. mexicana* Llave & Lexarza) is now the type species for the genus *Calibrachoa*.

Classification of the current *Petunia* and *Calibrachoa* species is still in progress. New species are being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. While *Petunia* species bear a flower peduncle and one new stem from a node, *Calibrachoa* species bear a flower peduncle and three stems. *Petunia* species have a cochlear corolla bud, a single outermost petal which covers the other four, and radially folded and terminally contorted petals. *Calibrachoa* flower buds are flat with all five petals linearly folded with the two lower petals forming a cover around the three other petals and fused together.

DESCRIPTION OF PHOTOGRAPH

This new *Calibrachoa* plant is illustrated by the accompanying photograph which shows blooms, buds, and foliage of the plant; the colors shown are as true as can be reasonably obtained by conventional photographic procedures. The photograph is of a three-month-old plant grown in a lexan-covered greenhouse.

FIG. 1. shows overall plant habit while the inset photograph shows a closer view of the mature flower.

DETAILED DESCRIPTION OF THE NEW PLANT

The following detailed descriptions set forth the distinctive characteristics of 'Cal Oran'. The data which defines these characteristics were collected from asexual reproductions carried out in Gilroy, Calif. The plant history was taken on four-month-old plants grown in one-gallon pots in a poly-covered greenhouse during the summer season. Color references are primarily to The R.H.S. Colour Chart of The Royal Horticultural Society of London (R.H.S.) (2001). Texture description data were collected by viewing plant parts with a dissecting microscope.

Classification:
- *Family.*—Solanaceae.
- *Species.*—*Calibrachoa* sp.

Growth:
- *Form.*—Semi upright and decumbent.
- *Growth and branching habit.*—Good vigorous habit, well branched full plant, somewhat upright.
- *Height.*—10–12 cm.
- *Width.*—50–65 cm.
- *Time to produce a finished flowering plant.*—8–10 weeks.
- *Outdoors plant performance.*—Does well in full sun; free flowering through the summer; some heat tolerance. Used as a hanging plant or in mixed containers.
- *Time to initiate and develop roots.*—18–23 days.

*Root description.*—White, fibrous.

Stems:
- *Color.*—RHS 144B.
- *Length.*—45–55 cm.
- *Diameter.*—0.15 cm.
- *Internode length.*—1.0–2.0 cm.
- *Texture.*—Glandular hairs of various sizes.
- *Anthocyanin.*—Reddish-purple.
- *Peduncle.*—Color: RHS 144B. Length: 2.0–2.6 cm. Diameter: 1.0 cm. Texture: Glandular hairs of various sizes.

Leaves:
- *Arrangement.*—Alternate; upper leaves sub-opposite.
- *Leaf color.*—Upper surface: RHS 137A. Lower surface: RHS 137C.
- *Length.*—4.0–4.2 cm.
- *Width.*—1.5–1.8 cm.
- *Shape.*—Oblong/broadly elliptic.
- *Martin.*—Entire.
- *Apex.*—Obtuse.
- *Base.*—Acuminate.
- *Texture.*—Sparse glandular hairs.
- *Venation.*—Pinnate.
- *Venation color.*—RHS 144B.
- *Petiole.*—Color: RHS 144B.
- *Length.*—0.2–0.3 cm.
- *Width.*—0.15 cm.
- *Texture.*—Sparse glandular hairs.

Flower bud:
- *Color at tight bud.*—RHS 162C.
- *Bud shape.*—Oblong.
- *Bud diameter.*—0.4 cm.
- *Bud length.*—1.4–1.7 cm.

Inflorescence:
- *Blooming habit.*—Continuous throughout the growing season. Good floriferousness.
- *Lastingness of individual blooms.*—5–8 days.
- *Fragrance.*—None.
- *Inflorescence type.*—Flowers solitary in upper leaf axis.
- *Flower type.*—Funnel form, 5 lobed petals, fused at base. Flower diameter.—3.2 cm.

Flowers:
- *Immature flower.*—Color: Shades of RHS 33A and RHS 33B. Veins: RHS N34A. Secondary veins: RHS 34A. Diameter: 2.6 cm
- *Mature flower color.*—Upper surface: Shades of RHS 32C and RHS 33C. Veins: RHS N34A. Secondary veins: RHS 32A. Underside: RHS 23C. Depth: 1.8 cm.
- *Corolla.*—Tube color inside: RHS 13B; veins RHS 177B. Tube color outside: Closest to RHS 23C with veins of RHS 177A and 177B. Tube length: 1.3 cm. Tube diameter at opening: 0.8 cm. Texture: Glandular hairs of various sizes.
- *Petals.*—Shape: Spathulate. Apex: Slightly retuse. Base: Fused. Margin: Entire. Length: 1.2 cm. Width: 1.4 cm. Waviness of petals: None. Lobation: Moderate. Texture: Papillose.
- *Sepals: Number:* 5. Color: RHS 143B, Lower surface. Length: 1.2–1.3 cm. Width: 0.35 cm. Shape: Oblong. Apex: Acute. Margin: Entire. Texture: Glandular hairs of various sizes.

Reproductive organs:
- *Stamens.*—5; 2 taller, 3 shorter.
- *Filament color.*—RHS 145D.
- *Pollen color.*—RHS 5B.
- *Pistil.*—1.
- *Length.*—1.3 cm.
- *Stigma color.*—RHS 143C.
- *Style color.*—RHS 143D.
- *Fruit/seed set.*—Not observed Disease and insect resistance: Not observed.

COMPARISON WITH KNOWN CULTIVARS

'Cal Oran' differs from the female parent 367-1 (unpatented) by having darker leaves, a more prostrate habit and larger, more orange-colored flowers than 367-1. 'Cal Oran' differs from the male parent 455-1 (unpatented) by having smaller leaves and more orange-colored flowers and being earlier to flower than 455-1.

'Cal Oran' differs from the commercial variety 'Mini Famous Apricot' (U.S. Plant Pat. No. 14,172, known in the patent as 'KLECO1061') by having a more upright habit, larger and darker green leaves, and a darker orange flower.

What is claimed is:

1. A new and distinct *Calibrachoa* plant as shown and described herein.

* * * * *